United States Patent
Wiemker et al.

(10) Patent No.: US 9,678,620 B2
(45) Date of Patent: Jun. 13, 2017

(54) WORKFLOW FOR AMBIGUITY GUIDED INTERACTIVE SEGMENTATION OF LUNG LOBES

(71) Applicant: KONINKLIJKE PHILIPS N.V., Eindhoven (NL)

(72) Inventors: Rafael Wiemker, Kisdorf (DE); Thomas Blaffert, Hamburg (DE); Cristian Lorenz, Hamburg (DE); Daniel Bystrov, Hamburg (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 472 days.

(21) Appl. No.: 14/349,096

(22) PCT Filed: Oct. 1, 2012

(86) PCT No.: PCT/IB2012/055241
§ 371 (c)(1),
(2) Date: Apr. 2, 2014

(87) PCT Pub. No.: WO2013/054224
PCT Pub. Date: Apr. 18, 2013

(65) Prior Publication Data
US 2014/0298270 A1 Oct. 2, 2014

Related U.S. Application Data

(60) Provisional application No. 61/545,605, filed on Oct. 11, 2011.

(51) Int. Cl.
*G06F 3/0481* (2013.01)
*A61B 6/00* (2006.01)
(Continued)

(52) U.S. Cl.
CPC .......... *G06F 3/04815* (2013.01); *A61B 6/466* (2013.01); *G06F 3/04842* (2013.01);
(Continued)

(58) Field of Classification Search
None
See application file for complete search history.

(56) References Cited

U.S. PATENT DOCUMENTS 6,993,174 B2 * 1/2006 Fan ........................... G06T 7/11
382/131
7,009,611 B2 * 3/2006 Di Lelle ............... G06F 17/211
345/420
(Continued)

FOREIGN PATENT DOCUMENTS

CN 101065773 10/2007
WO 2009157946 A1 12/2009

OTHER PUBLICATIONS

Bornik, A., et al.; Interactive Editing of Segmented Volumetric Datasets in a Hybrid 2D/3D virtual Environment; 2006; ACM; pp. 197-206.

*Primary Examiner* — Tsung-Yin Tsai

(57) ABSTRACT

An apparatus and a method for post processing 2D image slices (110*a-c*) defining a 3D image volume. The apparatus comprises a graphical user interface controller (160), a 2D segmenter (170) and a 3D segmenter (180). The apparatus allows a user to effect calculation and display of a 2D segmentation of a cross section of an object shown in a slice (110*a*) and calculation and display of a 3D segmentation of the object across the 3D image volume, the 3D segmentation based on the object's previously calculated 2D segmentation.

17 Claims, 3 Drawing Sheets

(51) Int. Cl.
*G06F 3/0484* (2013.01)
*G06T 7/174* (2017.01)

(52) U.S. Cl.
CPC .... *G06T 7/174* (2017.01); *G06T 2207/10081* (2013.01); *G06T 2207/20101* (2013.01); *G06T 2207/30061* (2013.01)

(56) References Cited

U.S. PATENT DOCUMENTS

| | | |
|---|---|---|
| 7,548,649 B2 | 6/2009 | Cardenas et al. |
| 7,660,451 B2 | 2/2010 | Reeves et al. |
| 7,739,623 B2 * | 6/2010 | Liang ................ G06T 19/00 382/128 |
| 2002/0168618 A1 * | 11/2002 | Anderson ................ A61F 2/07 434/262 |
| 2005/0231530 A1 * | 10/2005 | Liang ................ G06T 19/00 345/619 |
| 2005/0276455 A1 | 12/2005 | Fidrich et al. |
| 2008/0260221 A1 * | 10/2008 | Unal ................ G06K 9/342 382/128 |
| 2010/0021026 A1 * | 1/2010 | Collins ................ G06K 9/00 382/128 |
| 2010/0153076 A1 * | 6/2010 | Bellettre ................ G06T 7/33 703/2 |
| 2010/0208963 A1 * | 8/2010 | Kruecker ................ G06T 3/0081 382/131 |
| 2013/0021372 A1 * | 1/2013 | Wiemker ................ G06T 7/0012 345/629 |

* cited by examiner

WORKFLOW FOR AMBIGUITY GUIDED INTERACTIVE SEGMENTATION OF LUNG LOBES

CROSS REFERENCE TO RELATED APPLICATIONS

This application is a national filing of PCT application Serial No. PCT/IB2012/055241, filed Oct. 1, 2012, published as WO 2013/054224 A1 on Apr. 18, 2013, which claims the benefit of U.S. provisional application Ser. No. 61/545,605 filed Oct. 11, 2011, which is incorporated herein by reference.

FIELD OF THE INVENTION

The present invention relates to an apparatus for post processing 2D cross sectional slice images, to a method for post processing 2D cross sectional slice images, to a computer program element and to a computer readable medium.

BACKGROUND OF THE INVENTION

In computer aided diagnosis segmentation tools are used to segment images of medical objects into sub-objects representing relevant physiological features of the object. Examples are COPD (chronic obstructive pulmonary disease) and lung cancer diagnosis segmentation tools that are used to segment a CT (computed tomography) image volume of a left or right lung into its lung lobes.

Fully automated segmentation algorithms are known but do not always yield the desired results. Segmentations so produced will then have to be reviewed and corrected or edited which can be at times cumbersome. This is particularly true for higher than two dimensional segmentations.

SUMMARY OF THE INVENTION

There may therefore be a need to better support medical practitioners in handling computer generated (or otherwise) segmentations of objects represented by medical image data.

The object of the present invention is solved by the subject matter of the independent claims. Further embodiments are incorporated in the dependent claims.

It should be noted that the following described aspects of the invention equally apply to the method of processing 2D cross sectional slice images, to the medical system for post processing 2D cross sectional slice images, for the computer program element and to the computer readable medium.

According to one aspect of the present invention there is provided an apparatus for post processing 2D cross sectional slice images defining a 3D image volume data set. The apparatus comprises:
  a graphical user interface controller;
  a 2D segmenter; and
  a 3D segmenter.

The graphical user interface controller is configured to generate for display on a screen a graphical user interface. The user interface when so displayed comprises an interactive first window widget displaying on the screen an initial slice from among the 2D slices. The slice shows a cross section of an object of interest, the window widget configured to allow a user to specify by a pointer tool position data of a single initial point anywhere on the displayed initial slice.

The 2D segmenter is configured to 2D segment, in response to the user so specifying the position data, the displayed initial slice by calculating across the slice a curvilinear segmentation line passing through or starting at the specified single initial point.

The graphical user interface controller is further configured to generate for display in the first window widget the calculated segmentation line overlaid on the initial slice.

The 3D segmenter is configured to calculate, in response to a user request, a 3D segmentation of the object across a plurality of the 2D slices making up the 3D image volume by using the calculated segmentation line as a (geometric or cross sectional) constraint.

The graphical user interface controller is further configured to generate for display on the screen at least a part of the so calculated 3D segmentation.

The apparatus provides interactive 2D and 3D segmentation review for cases where the apparatus suggested segmentation results should turn out not to be satisfactory.

The apparatus also allows easily effecting 2D segmentation of, for example, a lung's slice image t into image portions representing the lobar footprints. A 3D segmentation of the lung's 3D footprint across the 3D image volume is then computed from boundary constraints defined by the previously calculated 2D segmentation. The 2D segmentation may include segmentation lines representing the lung's fissure lines and a contour outlining the lung's footprint boundary. The segmentation lines together with parts of the contour then form the lung lobe footprint segments.

The 2D segmentations are calculated and the GUI controller then effects their display in the window widget. It is only when the user "click" approves the semi-automatically generated 2D segmentation that the 3D segmentation is computed based on the approved 2D segmentation. So the apparatus affords the user to determine from which 2D segmentations the 3D segmentation is to be build. The apparatus is semi-automatic rather than fully automatic because the user still must provide the initial point for the 2D segmentation. However there is only a single point that needs to be specified by the user. Because the apparatus implements this single initial point based 2D segmentation, little user interaction is needed and quick workflow is secured with user distraction kept at a minimum.

According to one embodiment of the present invention the calculated segmentation line is stored in a buffer upon the user requesting the 3D segmentation. Upon the user specifying a new initial point, the segmenter calculates a new segmentation line passing through the new initial point. The newly calculated segmentation line is then displayed along with the previously calculated segmentation line in the first window widget overlaid on the initial slice. Upon the user requesting calculation of a new 3D segmentation, the new segmentation line is also stored along with the previous segmentation line in the buffer. The segmenter then uses as constraints both of the so buffered segmentation lines to calculate a new 3D segmentation of the object. The graphical user interface controller then updates the screen to now display the lung's newly calculated 3D lobe segmentation.

After the user positions the mouse cursor on the displayed slice near a visible fissure line, mouse click effects in sub-second calculation/CPU time the 2D segmentation and prompt graphical rendering of the so calculated 2D segmentation line in the first window widget. Once the user changes the mouse position again, a new 2D segmentation solution is suggested and displayed.

The user, if satisfied with the 2D segmentation results, can then accept the currently shown 2D segmentation by mouse click. Mouse click effects adding the 2D segmentation of the currently visible slice to the buffer of confirmed 2D segments. Buffering of the 2D segmentation allows the user to still later review the segmentations and allows each run of the 3D segmentation to account for all of the so far user approved 2D segmentations. According to one embodiment the 2D segmentation includes the fissure line segmentation line along with the lung's contour outline. Buffering of the 2D segmentation includes buffering a reference to the slice which is 2D segmented by the so calculated 2D segmentation.

Upon the user accepting the suggested 2D fissure segments, an updated 3D solution for the 3D segmentation is shown for each newly accepted 2D segmentation. The user can therefore by accepting step-by-step more and more 2D segmentations successively improve the quality or "fidelity" of the 3D segmentation solution to the true geometry of the lung and its lobes. 3D segmentations true to the lung's real footprint are thereby achievable in comparably short time.

According to one aspect of the present invention the graphical user interface controller is configured to generate for display in a second window widget the so calculated 3D segmentation. The controller effects display of the 3D segmentation in a second window widget different from the first window widget used for display of the slice-wise 2D segmentation.

The then generated graphical user interface is "two pane" and includes the first and second window widget as GUI components displayed inside a super window widget (a "container") or may be displayed without such common window on the screen as to two separate windows which each may be shifted by mouse-click-and-drag interaction independently from each other across the screen plane. In another embodiment a single window GUI is used alternatively displaying either the single slice 2D segmentation or a slice as part of the 3D segmentation.

According to one embodiment, the graphical user interface controller is configured to generate for display a 3D rendering of the so calculated 3D segmentation.

Displaying of the 3D segmentation may be complete in that a full 3D, interactively rotatable, 3D rendering is displayed or the displaying may be partial in that one of a slice-wise 2D cross section of the 3D segmentation is displayed According to one embodiment of the present invention the pointer tool is a computer mouse and the specifying of the position data or the new position data is effected without using a mouse click event but by using position recordings generated by the mouse as the mouse is moved by the user. In contrast, the user request for the 3D segmentation and the buffering of the 2D segmentations is effected by both, mouse click and by using the position readings.

User required interaction via the pointer tool (computer mouse or light pen or similar) with the apparatus are further minimized by the zero-click implementation thereby furthering yet again quick work flow in the ever more competitive clinical environment. The 2D segmentations are suggested to the user by merely letting the mouse cursor "hover" over selected slice reformats.

For the user apparently occurring at substantially the same instant, triggered by the mouse click for accepting the currently displayed 2D segmentation, the 3D segmentation of the lung's footprint across the 3D image volume is computed and is then at least partly displayed.

According to one embodiment of the present invention the segmenter is configured to calculate in addition to the requested 3D segmentation at least one further sample 3D segmentation. The sample 3D segmentation is based on at least one sample region in the 3D volume not used in the calculation or not forming part of the requested 3D segmentation. The apparatus further comprises a comparator configured to compare the requested 3D segmentation with the sample 3D segmentation to establish a deviation value. The comparator is configured to issue, when the deviation value exceeds a configurable threshold value, a command to the graphical user interface controller to update the first window widget to then display a slice showing a cross section of the so identified sample region.

This functionality affords automatically pointing the user's attention to a slice or reformat from among the slices of the 3D volume which contains a 3D region of high or highest "algorithmic ambiguity". This is a region that would have caused the largest (a larger than a preset value) deviation from the 3D segmentation currently displayed if this region had been included in the 3D calculation of the currently displayed 3D segmentation. Deviation is measured with respect to a suitable deviation measure which allows comparing the 3D image volume portions forming the respective 3D segmentations.

Internal decision nodes or points in the decision tree of the used 3D segmentation algorithm are analyzed to identify the lung region having the largest or a large logarithmic ambiguity. Relevant internal decision points in the algorithm are those that would have led to a change in the 3D segmentation outcome, had the algorithm at this point been executed along a different path than the one that has led to the currently viewed 3D segmentation. According to one embodiment, the decision point analysis can be implemented by exploring not merely one but a plurality of 3D segmentation solutions associated with different ones of local minima of a functional solved for by the algorithm.

Analysis of the 3D segmentation algorithm is carried out in the background and once completed, the first window widget for the slice-wise display is updated or reset to now display instead of the previous slice a slice through the so established region of high ambiguity. According to one embodiment the slice is selected to intersect the region at its center. This selection includes scrolling and possibly rotation to effect display of the region of largest ambiguity. The user can then accept by mouse click and add to the buffer the now shown slice indicating the region of high or highest ambiguity. The slice is then used as a valid constraint for the 3D segmentation.

The apparatus allows the user to sample some or all of the other 3D segmentation solutions so the final decision on the medically most appropriate solution truly rests with the user. In effect the user can control the execution of the 3D segmentation algorithm to more fully "sample" the whole of the 3D image volume for solutions to the current 3D segmentation problem.

The apparatus according to the present invention allows the user to comfortably review with as few user actions as possible the proposed 3D slice segmentation. The user is supported in finding a possibly better 3D segmentation solution by the apparatus suggesting slices for 2D segmentation which may otherwise not have considered. The likelihood that the user captures the full physiological geometry of the lung to be examined can thereby be increased because the solution space across the 3D volume set is better sampled. The user is guided to meaningfully constrain the calculation of the 3D segmentation by 2D slices that actually add information about the true geometry of the lung or object of interest. In short, the apparatus affords interactive algorithmic ambiguity guided 3D segmentation.

The apparatus may be used in imaging work stations and PACS for screening diagnosis and therapy monitoring for COPD and lung cancer applications.

DEFINITIONS

Segmentation is the partitioning of hitherto unstructured pixel or voxel information in a slice into pixel or voxel regions. The regions can then be treated as objects in their own right. Each pixel or voxel in the image can then be said to be either inside or outside the object. Each object or objects into which an image has been partitioned into is referred to as "a segmentation".

A segmentation is said to be 2D if the regions are confined to the image slice plane of a single slice. The segmentations can then be defined by one or more curvilinear boundaries.

A segmentation is said to be 3D if the regions extend across a collection of slices in the 3D image volume, the 3D segmentation then being defined by a 2D segmentation in each of those slices. The 3D segmentations can then be defined by one or more surfaces. The surfaces or curvilinear lines defining the 3D or 2D segmentations are likewise referred to as the "segmentation" or "segmentation surface" or "segmentation line".

A real object's footprint in an image is the set of pixels or voxels together representing that object.

A decision node in the algorithm's decision tree is ambiguous if at that node there existed more than one solution for a suitable 3D segmentation and the algorithm proceeds along one of at least two possible execution paths and outputs one of the solutions.

In extension of the concept of ambiguous decision points, a region of the 3D image volume is called ambiguous if it forms part of one of the 3D segmentation solution but does not form part of the other solution. And finally, a region has a higher ambiguity than another if a 3D segmentation having that region deviates more from the currently displayed 3D segmentation than any other 3D segmentation not having that region.

BRIEF DESCRIPTION OF THE DRAWINGS

Exemplary embodiments of the invention will be described in the following with reference to below drawings in which.

DETAILED DESCRIPTION OF EMBODIMENTS

Figure 1:
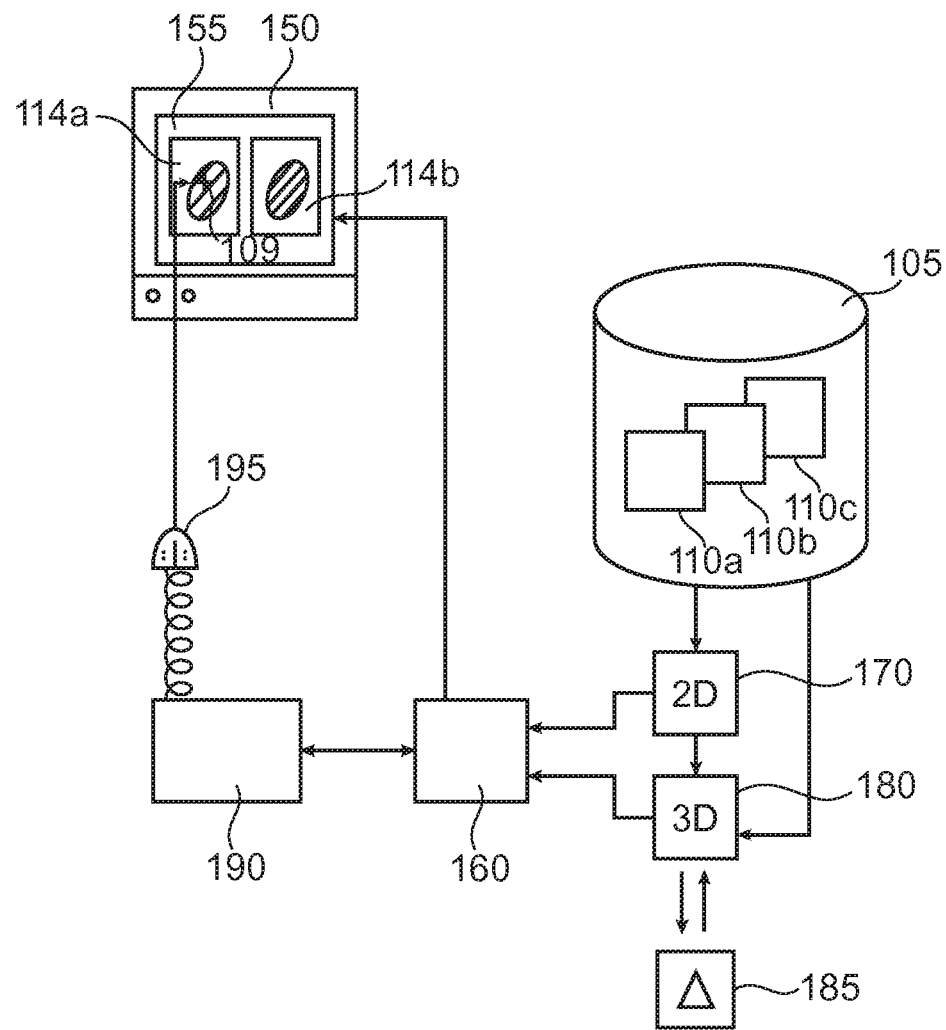
FIG. 1 schematically shows a block diagram of an apparatus for post processing 2D cross sectional slice images.

With reference to FIG. 1, the post processing apparatus comprises a data base 105 holding CT cross sectional slice images 110a-c defining a 3D image volume. One of the slices, for example slice 110a, can be displayed in a two pane graphical user interface 155 on a computer screen 150. The visual appearance of and the user interaction functionalities provided by the graphical user interface (GUI) 155 is controlled by GUI controller 160. The apparatus further comprises a 2D segmenter 170 and a 3D segmenter 180. There is also a comparator 185 in communication with 3D segmenter 180. The apparatus further comprises a processing unit 190 such as a work station in communication with GUI controller 160, 2D segmenter 170, 3D segmenter 180 and comparator 185. There is also provided a pointer tool such as a computer mouse 195 in communication with processing unit 190 which allows a user to interact with GUI 155 under the control of GUI controller 160.

The components of the apparatus are shown spread out in FIG. 1. However, this is only for clarity of illustration. The apparatus components processing unit 190, 2D segmenter 170, 3D segmenter 180, and comparator 185 may indeed be locally distributed and connected in a suitable communication network. In other embodiments however the components 170, 180 and 185 are running as software routines on the processing unit 190. The components may also be arranged as dedicated FPGAs or hardwired standalone chips. The components may be programmed in a suitable scientific computing platform such as Matlab® or Simulink® and then translated into C++ or C routines maintained in a library and linked when called on by processing unit 190.

Broadly speaking, the apparatus in FIG. 1 aids the user such as a radiologist in generating 2D and 3D segmentations of an object of interest such as a left or right human or animal lung. Segmentation in this case may include segmenting the overall cross sectional contour of say the left lung and segmentations of the superior and inferior lung lobes making up the left lung. However it is understood that the object of interest may be a different physiological part of an animal or human organism and segmentation would then be directed to different physiological features.

The 3D segmentation is based on 2D segmentations of one or more of the slice images 110a-c. The apparatus also helps the user in 2D segmenting the one or more slice images. The slice 110a along with its 2D segmentation is displayable in the left pane formed by a first window widget 114a. At least a partial representation of the 3D segmentation of the lung lobe based on the previously calculated one or more 2D segmentations is displayable in the second pane formed by a second window widget 114b. The user can interact via mouse 195 with the graphical user interface 155 by issuing interaction events. GUI controller then intercepts those interaction events and issues corresponding commands to a system graphic card (not shown) to so control display on the screen of the two GUI window widgets 114a, 114b.

Figure 2:
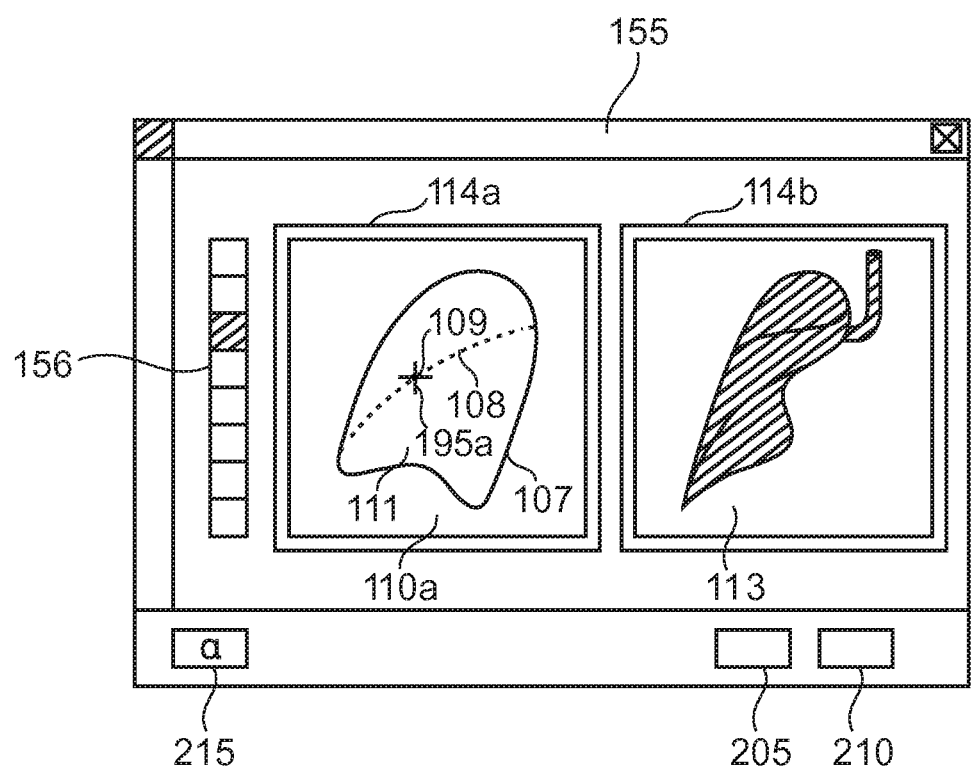
FIG. 2 shows a graphical user interface for post processing 2D cross-sectional slice images.

The user can actuate a load button 205 (see FIG. 2) to load for viewing a suitable slice 110a into first window widget 114a. The user can then adjust the projection angle across the 3D volume by actuating "alpha" button 215 or he may scroll by means of a slide bar 156 through the slices 110a-c held in the data base 105 to view another one of the slices for 110a-c. By using slide bar 156 of GUI 155, the radiologist scrolls through the slice images 110a-b which are then displayed one at a time in the left pane window 114a. The slices are preferably displayed as sagittal reformats with a slice thickness of about 1-5 mm. Preferably the rotation angle alpha around the cranio-cordal axis (formed by the intersection between the sagittal plane and coronial plane) and the slice thickness can be adjusted by actuating "alpha" button 215 or a "config" button 210. Invoking config button 210 or alpha button 215 effects a "config" pop up window to be temporarily overlaid the on graphical user interface 155. User may then tick box or key in the desired configuration parameter such as slice thicknesses, rotation angle or a position in the 3D volume of the slice 110a-b he or she wishes to view.

The apparatus allows the user to initiate the 2D segmentation by selecting a single point on the currently displayed slice 110a. The position data of the single point is generated by movement of the mouse pointer and is then passed on via GUI controller 160 to 2D segmenter 170. 2D segmenter 170 then generates a segmentation line 108 (see FIG. 2) starting at or passing through the initial single point 109 specified by the user by positioning "hair cross" mouse cursor 195a as exemplary shown in FIG. 2.

This semi-automatic 2D segmentation of the shown lung into two lobes (that is the portion above (superior lobe) and below (inferior lobe) the segmentation line 108) also includes generating an outer contour line 107 of the left lung's footprint currently shown in slice 110a. Segmentation line 108 traces out the more or less visible lobar fissure line as shown in slice 110a. Specification of the initial single point 109 is by zero click interaction. In other words, when the mouse cursor 195a is not moved after its positioning for a pre-determined time limit, the segmentation line 108 based on the currently pointed to position is automatically generated by 2D segmenter 170. No mouse click action is required by the user to have the 2D segmentation executed. The user merely lets the mouse courser 195a "hover" over the image plane. The segmentation line 108 is then based on the then pointed to single point 109. The pre-determined delay can be configured by using "config" button 210.

The generated 2D segmentation line 108 either starts at the initial point 109 and extends to the left or to the right to intersect lung contour 108 at only one point or segmentation line 108 passes through the initial segmentation 109 and intersects outer contour line 107 at two opposite points. The apparatus can be configured accordingly by actuating config button 205.

A graphical rendering of the calculated 2D segmentation is then displayed overlaid on the currently displayed slice 110a in window 114a. The graphical rendering includes components for the segmentation line 108 and the contour 108. If the automatically generated 2D segmentation as shown in left pane window 114a is to the user's satisfaction, the user issues a confirming mouse click event whereupon the currently displayed 2D segmentation, that is the outer contour 107 and the segmentation line 108, is saved in a buffer. Along with saving the 2D segmentation there is also stored in the buffer a reference to the slice (in this case slice 110a) which is segmented by the so calculated 2D segmentation. If the user changes mouse position without issuing a confirming mouse click event the currently displayed 2D segmentation is discarded and a new segmentation is calculated and rendered for display should the mouse cursor reside at the new position longer than the pre-set delay.

Upon confirming by mouse click the 2D segmentation, a 3D segmentation across the 3D volume data set is generated by 3D segmenter 180, the 3D segmentation then being based on the confirmed 2D segmentation. The 3D segmentation 113 or at least a partial representation thereof is then shown in the second window widget 114b. The user can then scroll by using slide bar 156 or key strokes to another slice 110b and effect similar 2D segmentations of the then shown slice 110b in window widget 114a. Again, once the user is satisfied with the system suggested 2D segmentation shown on the now displayed new slice 110b, a corresponding segmentation line and its contour are likewise stored in the buffer upon mouse click action. Upon storing 2D segmentation for the second slice 110b in the buffer, 3D segmentation window 114b is updated and a new 3D segmentation is shown this time being based on all of the 2D segmentations stored in the buffer. The buffered 2D segmentations define geometric constraints for the 3D algorithm implemented by 3D segmenter 180.

The 3D segmentation 113 of lung footprint may be displayed as a 3D rendering by a renderer (not shown) or may be represented by one of the slices from the 3D volume forming the 3D segmentation, the slice having overlaid the corresponding sectional 2D segmentation of the full 3D segmentation. In this embodiment GUI 155 may include a further slide bar which would allow the user to scroll through the collection of slices forming the 3D segmentation. Each slice when so displayed in right pane 114b has then its corresponding sectional 2D segmentation overlaid. In yet another embodiment, GUI 155 comprises a single window widget which alternately shows either the 2D segmentation of a single slice or of the slices of the collection of slices forming the 3D segmentation each slice then with the corresponding 2D segmentation overlaid. Alternatively, the 3D rendering of the 3D segmentation is displayed in the single window. In the single window embodiment, user can toggle between single slice 2D segmentation view or 3D segmentation view.

By reviewing and confirming slice by slice the 2D segmentations shown in window 114a, the user can in a "collection phase" collect and so accumulate suitable 2D segmentations to so define a "stockpile" of geometrical constraints which are then used in combination by the 3D segmenter 180. This allows the user to gradually choose better or more suitable 2D segmentations displayed one at a time in the left pane of the graphical user interface 155 and gradually generate improved 3D segmentations 113 displayed in the right pane 114b of GUI 155. The 2D cross-sectional constraints for the 3D segmentation collected in the "collection phase" are each quality control reviewed by visual inspection in left pane 114a and the actual 3D segmentation is then executed in a later "3D segmentation phase" and is then displayed for visual inspection in right pane 114b.

Operation

The current mouse position specifying the position data of the single point 109 is passed to 2D segmenter 170 as a starting or through point for calculating the fissure line tracing segmentation line 108. 2D segmenter 170 uses pattern recognition and/or gradient based methods to determine suitable directions from the specified single point 109 across the image plane currently displayed in slice 110a. To this end, candidate directions forming a star-shaped family of vectors emanating from the single initial point 109 are defined. The lobar fissure line is expected to have lower voxel intensity as compared to the voxel regions on either side of the fissure line. This voxel intensity pattern calls for a steep gradient rise across the fissure line direction to either of its side. 2D segmenter chooses from among a collection of candidate directions a direction best matching this expected gradient characteristic.

Once a suitable direction that best matches the expected gradient characteristic is found, a new coordinate point for the to be calculated segmentation line is chosen at a suitable distance along that direction and the previously described procedure for choosing the suitable candidate direction is repeated. The distance is a "step width" which is configurable and reflects the resolution required in the calculation of the 2D segmentation. In this fashion, 2D segmenter 170 point by point calculates and so iteratively traces out the lobar fissure line and produces a co-ordinate description of segmentation line 108.

2D segmenter proceeds in a similar fashion to calculate the contour line 108 by defining suitable contour line candidates and using voxel intensity gradient values to trace the lung's footprint boundary. In one embodiment the voxel grey value intensities along the calculated segmentation line are recorded. A point on the line at which a sudden drop in grey value intensity occurs is interpreted as the intersection point between the segmentation line and the boundary of the lung's footprint in the slice. Based on that intersection point, contour 108 can then be calculated using known edge detection algorithms.

The so calculated coordinates of the segmentation line 108 and the contour 107 together forming the 2D segmentation are then passed to GUI controller 160 which then causes or effects display of the 2D segmentation as a graphical element in window widget 114a. The 2D segmentation, that is outer contour 108 and segmentation line 107, is displayed as overlay graphics overlaid on the currently displayed slice 110a.

The 2D segmentation conforming mouse click event also causes the co-ordinate description of the 2D segmentation to be stored in the 3D segmentation constraints buffer. In this way the buffer defines a "clip-board" for a list of confirmed 2D segmentations. According to one embodiment GUI 155 provides buttons to enable the user to review the clipboard buffer. The buffer is updated gradually and builds up a collection of user approved 2D segmentations as the user changes mouse position across left window pane 114a and issues confirming mouse click events.

Each mouse click event for storing the currently viewed 2D segmentation triggers a 3D segmentation carried out by 3D segmenter 180. 3D segmenter 180 then uses all of the currently buffered slice wise 2D segmentations as a combined constraint to calculate the 3D segmentation of the lung across the 3D volume data set defined by the collection of slices 110a-d. So changing the mouse position and choosing a new initial single segmentation point in left pane 114a effects an update of the 3D segmentation displayed in the right pane 114b if the user accepts the currently viewed 2D segmentation 114a by mouse click in left pane 114a.

3D segmenter 180 implements suitable 3D segmentation algorithms. The algorithms can be expressed as finding solutions to a functional defined on the 3D volume data set constrained by the buffered 2D segmentations. Each possible 3D segmentation must have any one of the buffered 2D segmentations as its cross-section in respective ones of slices 110a-c. 3D segmenter extrapolates from cross sections defined the buffered 2D segmentations into other slices in the 3D volume set to so establish "missing" cross sections in those other slices. The 3D segmenter uses pattern recognition techniques to find the slices having foot prints best matching in voxel intensity and shape the buffered 2D segmentations. The footprints in the matched slices are then 2D segmented.

Each 3D segmentation solution is therefore formed by a collection of 2D segmentations. The collection includes the previously buffered 2D segmentations and the 2D segmentations of the matched slices. The collection of slices defines the 3D voxel region making up the 3D segmentation. This 3D voxel region can be expressed as a local minimum "point" of the functional. Local minima may be found by solving for zeros of the gradient of the functional. The functional is a real valued function defined on the 3D image volume or a coarse grained version of the volume. The coarse graining aspect will be explained in more detail below.

There is normally a large number of solutions. The 3D segmentation algorithm therefore uses a decision tree to output a single one of the solutions. A reference to the output solution is then passed on to GUI controller 160. GUI controller 160 then effects display of the output 3D segmentation solution in right pane 114b.

According to one embodiment the 3D segmenter 180 solves the functional for local minima across all suitable voxels region of the 3D volume data set.

According to a preferred embodiment however, to save CPU time, the possible solution space is restricted by a sphere commensurate with the expected dimensions (length, width and thickness) of the lung to be 3D segmented.

In yet another embodiment, the voxels inside the so defined sphere or the whole 3D volume are or is coarse grained into voxel "chunks" or individual 3D regions from which the 3D segmentation of the lung's 3D footprint can then be build up. According to one embodiment, 3D segmenter 180 carries out a course graining of the 3D volume data in a discretization phase prior to the calculation of the 3D segmentation. 3D segmenter 180 analysis for each chunk whether it includes a cross section slice for which a 2D segmentation can be constructed that can be fitted in voxel grey value intensity and shape to the collection of buffered 2D segmentations. If the 2D segmentation can be fitted, the chunk is flagged up and then forms part of the 3D segmentation solution.

Such a coarse graining can for example be guided by harnessing physiological facts about lungs or the particular organ of interest. One way to define the 3D chunks is to pre-segment the 3D image volume around the lung's footprint into portions representing lung blood vessels. The blood vessels are known not to extend across the fissure lines but are confined, for the left lung case, to either one of the two lobes. The constraints defined by the segmentation lines in the buffered 2D segmentations can be used for this coarse graining and no chunk is allowed to cross the fissure lines representing the segmentation lines. Solving the 3D segmentation functional across those 3D blood vessel chunks would then ensure that physiological realties are respected.

According to one embodiment of the present invention the apparatus guides the user in choosing 2D segmentation constraints in left pane 114a in a manner to best capture the geometry of the to be 3D segmented lung. To this effect segmenter 180 not only outputs for display a single 3D segmentation but also calculates further candidate 3D segmentation solutions for a configurable number of other local minima. The candidate 3D segmentation solutions corresponding to other local minima are calculated in the background but at this point are not displayed but instead are passed to comparator 185. Comparator 185 then establishes a deviation between the currently displayed 3D segmentation solution and each of the candidate 3D segmentations calculated in the background. According to one embodiment a measure of deviation is by establishing for each candidate solution and the currently displayed solution the volume ratio of the lung lobe footprints as defined by respective outer contours and segmentation lines in the slices making up the respective 3D segmentations.

The respective lobar volume ratios are than compared with the lobar volume ratio of the currently displayed solution. If one of the candidate solution's volume ratio is found to deviate from the lobar volume ratio of the currently displayed solution by more than a pre-set threshold deviation, the chunks making up the deviating solution and the chunks making up the currently displayed solutions are compared. At least one chunk is then identified in the deviating solution that is not part of the currently viewed 3D segmentation. Processing unit 190 then accesses data base 105 and selects a slice intersecting that chunk. A reference to the so identified slice, slice 110c say, from among the slices 110*a*-*c* of the 3D volume is then forwarded to GUI controller 160. GUI controller 160 then updates left pane 114*a* to now display slice 110*c* instead of slice 110*a*, slice 110*c* now showing a cross-section of the identified chunk that may have caused the deviation. According to another embodiment the deviating chunk may simply be chosen to be one the furthest away from the chunks making up the currently displayed 3D segmentation solution.

So the apparatus allows the user to be made aware of an "ambiguous" lung region that would have caused display of a largely different 3D segmentation had the 3D segmentation algorithm decided to output a solution comprising that chunk. In this way the apparatus supports the user and encourages him or her to more widely spread the choice for the 2D segmentation constraints across the whole of the 3D volume to so stand a better chance to capture the true geometry of the to be 3D segmented lung into its lobes. The user may then proceed to 2D segment the so suggested and now displayed slice 110*c* showing the chunk with high ambiguity and to add that slice to the buffer. Upon so buffering the new 2D segmentation, the background calculated candidate 3D segmentation is then displayed instead of the previous 3D segmentation in the second window widget. Should the user be not satisfied with the so suggested 3D segmentation, a buffer button (not sown) of GUI 155 may be actuated effecting display of an overlay window as a clip board. The clip board overlay window includes a list of reference links to the buffered 2D segmentations and mouse clicking on the links would effect display in window 144*a* of the respective 2D segmentation overlaid on the respective on of the slices. The user can then struck out from the buffer the reference of the suggested 2D segmentation of the slice showing the high ambiguity chunk. Display in second window widget 114*b* then reverts to the previously shown 3D segmentation. According to one embodiment, the user can always and at any stage invoke the buffer clip-board and remove 2D segmentation constraints from the buffer and such removal will then effect updating the second window widget 114*b* to then show a 3D segmentation then based on the constraints remaining in the buffer.

Figure 3:
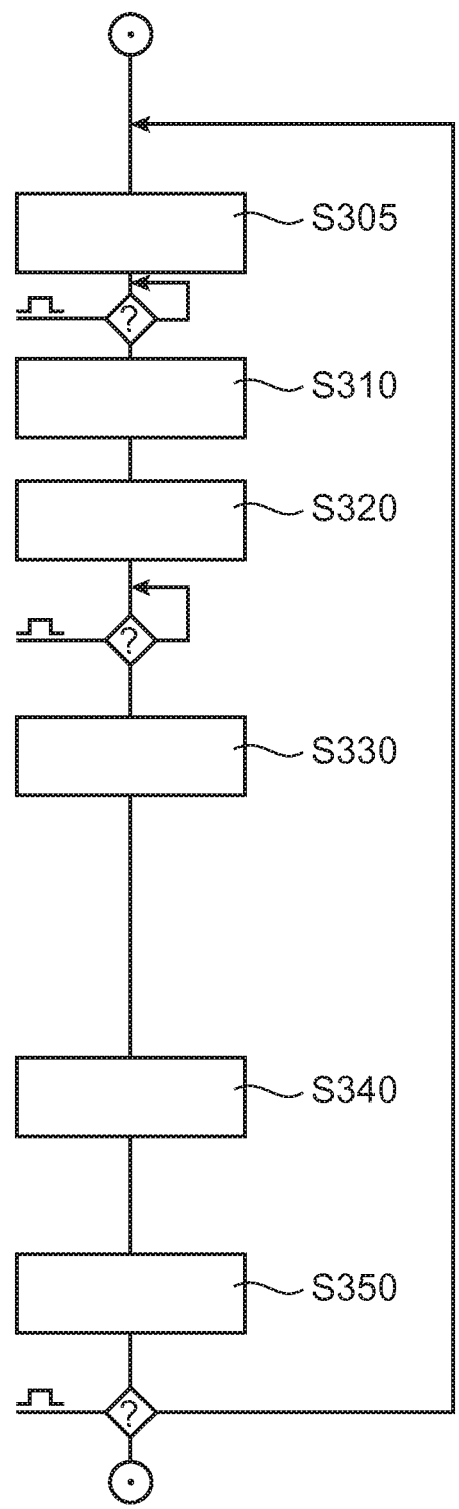
FIG. 3 schematically shows a flow chart for a method of post processing 2D cross sectional slice images.

With reference to FIG. 3, a flow chart is shown for a method of post processing 2D cross sectional slice images.

In step S305 an initial slice image is displayed in a first window widget of a graphical user interface.

In step S310 and in response to a user specifying in the displayed initial slice position data of a single initial point, a 2D segmentation is calculated of the displayed slice based on a curvilinear segmentation line passing through or starting at the specified single initial point.

In step S320 the so calculated 2D segmentation is rendered for display as a graphic overlaid on the initial slice and superposed along the footprint of the object to be segmented.

In step S330 and in response to a user request, the 2D segmentation is stored in a buffer and a 3D segmentation of the object's 3D footprint across the 3D image volume is calculated. The calculation of the 3D segmentation is based on the previously calculated 2D segmentation in the displayed 2D slice.

In Step s340 a at least partial graphic rendering of the so calculated 3D segmentation is displayed on the screen, either in a second window widget or instead of the slice in the first window widget.

In addition to the requested 3D rendering segmentation, a further 3D segmentation is calculated in the background. The further 3D segmentation is based on at least one sample region in the 3D image volume that has not been used in the calculation of the actually requested 3D segmentation. The two 3D segmentations are compared in step S350 and a deviation value between the two is established. If the deviation value exceeds a pre-set and configurable threshold value, the first window widget is updated by displaying the slice showing a cross section of the so identified sample region.

Steps S305 through S350 can then be repeated upon the user's specifying in the now shown slice or in a further slice yet a further single initial point for segmentation to thereby successively collect a set of 2D segmentation as constraints and successively re-calculate 3D segmentations based on all or a configurable number of the thus far collected 2D segmentations.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for post-processing 2D cross-sectional slice images defining a 3D image volume data set, the apparatus comprising:
    a graphical user interface controller;
    a 2D segmenter; and
    a 3D segmenter;
    wherein the graphical user interface controller is configured to generate for display on a screen a graphical user interface, the user interface when so displayed comprising an interactive first window widget displaying on the screen an initial slice of the 2D slices, the slice showing a cross section of an object of interest, the window widget configured to allow a user to specify by a pointer tool position data of a single initial point anywhere on the displayed initial slice;
    wherein the 2D segmenter is configured to 2D segment, in response to the user specifying the position data, the displayed initial slice by calculating across the slice a curvilinear segmentation line passing through or starting at the specified single initial point;
    wherein the graphical user interface controller is further configured to generate for display in the first window widget the calculated segmentation line overlaid on the initial slice;
    wherein the 3D segmenter is configured to calculate, in response to a user request, a 3D segmentation of the object across a plurality of the slices by using the calculated segmentation line as a geometric constraint for the 3D segmentation; and
    wherein the graphical user interface controller is further configured to generate for display on the screen at least a part of the so calculated 3D segmentation.

2. The apparatus according to claim 1, wherein the calculated segmentation line is stored in a buffer upon the user requesting the 3D segmentation, wherein upon the user specifying a new initial point, the segmenter calculates a new segmentation line starting at or passing through the new initial point, the newly calculated segmentation line then being displayed in the first window widget overlaid on the initial slice, wherein upon the user requesting calculation of a new 3D segmentation, the new segmentation line is stored along with the previous segmentation line in the buffer, the segmenter then using as constraints both of the so buffered segmentation lines to calculate the new 3D segmentation of the object, and wherein the graphical user interface controller updates the screen to display at least a part of the object's new 3D segmentation.

3. The apparatus according to claim 1, wherein the pointer tool is a computer mouse and wherein the specifying of the position data or the new position data is effected without using a mouse click event but by using position recordings generated by the mouse as the mouse is moved by the user and wherein the user request for the 3D segmentation and buffering the segmentation lines is effected by both, mouse click and by using the position readings.

4. The apparatus according to claim 1, wherein the segmenter is configured to calculate in addition to the requested 3D segmentation at least one further sample 3D segmentation based on at least one sample region in the 3D volume not used in the calculation or not forming part of the requested 3D segmentation, the apparatus further comprising:
    a comparator configured to compare the requested 3D segmentation with the sample 3D segmentation to establish a deviation value, and configured to issue, when the deviation value exceeds a configurable threshold value, a command to the graphical user interface controller to update the first window widget to display a slice showing a cross section of the sample region.

5. The apparatus according to claim 1, wherein the constraint or constraints include a contour curve outlining the object's cross section in the initial or new initial slice.

6. The apparatus according to claim 1, wherein the graphical user interface controller is further configured to generate for display in a second window widget the so calculated 3D segmentation.

7. The apparatus according to claim 1, wherein the object of interest is part of a human or animal lung and the segmentation line represents a fissure line between two lung lobes of the lung.

8. The graphical user interface when displayed on the screen by an apparatus according to claim 1.

9. A method of post processing 2D cross-sectional slice images, the method comprising:
    displaying on a screen an initial slice of the 2D slices, the slice showing a cross section of an object of interest, the window widget configured to allow a user to specify by a pointer tool position data of a single initial point anywhere on the displayed initial slice;
    in response to a user specifying position data of the single initial point on the displayed slice, calculating across the slice a curvilinear segmentation line passing through or starting at the specified single initial point;
    displaying in the first window widget the calculated segmentation line overlaid on the initial slice;
    in response to a user request, calculating a 3D segmentation of the object across a plurality of the slices by using the calculated segmentation line as a geometric constraint for the 3D segmentation; and
    displaying on the screen at least a part of the so calculated 3D segmentation.

10. The method according to claim 9, further comprising storing in a buffer the calculated 2D segmentation including the segmentation line;
    upon the user specifying a new initial point, calculating a new segmentation line starting at or passing through the new initial point the newly calculated segmentation line;
    displaying in the first window widget the newly calculated segmentation line overlaid on the initial slice;

upon the user requesting calculation of a new 3D segmentation, storing the new segmentation line along with the previous segmentation line in the buffer;

using as constraints both of the so buffered segmentation lines to calculate the new 3D segmentation of the object; and displaying at least parts of the object's new 3D segmentation.

11. The method according to claim 9, wherein the pointer tool is a computer mouse and wherein the specifying of the position data or the new position data is effected without using a mouse click event but by using position recordings generated by the mouse as the mouse is moved by the user and wherein the user request for the 3D segmentation and buffering the segmentation lines is effected by both, mouse click and by using the position readings.

12. The method according to claim 9, further comprising:

calculating in addition to the requested 3D segmentation at least one further sample 3D segmentation based on at least one sample region in the 3D volume not used in the calculation or not forming part of the requested 3D segmentation;

comparing the requested 3D segmentation with the sample 3D segmentation to establish a deviation value; and when the deviation value exceeds a configurable threshold value, displaying a slice showing a cross section of the sample region.

13. A medical system for post-processing 2D cross-sectional slice images, the apparatus comprising:

a data base for holding the 2D image slices;

an apparatus according to claim 1; and the screen for displaying the first and/or second window widget as output by the apparatus.

14. A non-statutory computer readable medium encoded with computer executable instructions which when executed by a processor cause the processor to:

generate for display on a screen a graphical user interface comprising an interactive first window widget displaying on the screen an initial slice of 2D cross-sectional slice images section of an object of interest defining a 3D image volume data set;

receive a first signal indicative of a single initial point anywhere on the displayed initial slice;

segment, in response to the signal, the displayed initial slice by calculating across the slice a curvilinear segmentation line passing through or starting at the specified single initial point;

display in the first window widget the calculated segmentation line overlaid on the initial slice;

calculate, in response to a second signal, a 3D segmentation of the object across a plurality of the slices using the calculated segmentation line as a geometric constraint for the 3D segmentation; and display on the screen at least a part of the calculated 3D segmentation.

15. The non-statutory computer readable medium according to claim 14, wherein the instructions further cause the processor to:

store in a buffer the calculated segmentation including the segmentation line;

upon the user specifying a new initial point, calculate a new segmentation line starting at or passing through the new initial point the newly calculated segmentation line;

display in the first window widget the newly calculated segmentation line overlaid on the initial slice;

upon the user requesting calculation of a new 3D segmentation, store the new segmentation line along with the previous segmentation line in the buffer;

use as constraints both of the so buffered segmentation lines to calculate the new 3D segmentation of the object; and display at least parts of the object's new 3D segmentation.

16. The non-statutory computer readable medium according to claim 14, wherein the pointer tool is a computer mouse and wherein the specifying of the position data or the new position data is effected without using a mouse click event but by using position recordings generated by the mouse as the mouse is moved by the user and wherein the user request for the 3D segmentation and buffering the segmentation lines is effected by both, mouse click and by using the position readings.

17. The non-statutory computer readable medium according to claim 14, wherein the instructions further cause the processor to:

calculate in addition to the requested 3D segmentation at least one further sample 3D segmentation based on at least one sample region in the 3D volume not used in the calculation or not forming part of the requested 3D segmentation;

compare the requested 3D segmentation with the sample 3D segmentation to establish a deviation value; and display a slice showing a cross section of the sample region when the deviation value exceeds a configurable threshold value.

* * * * *